United States Patent [19]

Guram et al.

[11] Patent Number: 6,034,286
[45] Date of Patent: Mar. 7, 2000

[54] PROCESSES FOR PRODUCING SATURATED ALCOHOLS

[75] Inventors: Anil Sakharam Guram, Hurricane; John Robert Briggs, Charleston; Kurt Damar Olson; Thomas Carl Eisenschmid, both of Cross Lanes; Diane Lee Packett, South Charleston; Erik Bruce Tjaden, Charleston, all of W. Va.

[73] Assignee: Union Carbide Chemicals & Plastics Technology Corporation, Danbury, Conn.

[21] Appl. No.: 08/950,600

[22] Filed: Oct. 16, 1997

Related U.S. Application Data

[63] Continuation-in-part of application No. 08/843,381, Apr. 15, 1997.

[51] Int. Cl.[7] ............................. C07C 29/04; C07C 29/03
[52] U.S. Cl. ............................................ 568/882; 568/909
[58] Field of Search ...................................... 568/882, 909

[56] References Cited

U.S. PATENT DOCUMENTS

| | | | |
|---|---|---|---|
| 3,239,566 | 3/1966 | Slaugh et al. | 260/604 |
| 3,660,493 | 5/1972 | Johnson et al. | 260/604 |
| 4,098,727 | 7/1978 | Haag et al. | 521/53 |
| 4,451,679 | 5/1984 | Knifton et al. | 568/909 |
| 4,469,895 | 9/1984 | Knifton et al. | 568/454 |
| 5,312,996 | 5/1994 | Packett | 568/454 |

FOREIGN PATENT DOCUMENTS

| | | |
|---|---|---|
| 0420510 | 4/1991 | European Pat. Off. . |
| 1254222 | 11/1971 | United Kingdom . |

OTHER PUBLICATIONS

J.M. Andersen, *Improved regioselectivity in the hydroformylation reaction catalysed by zeolite–encapsulated rhodium (I) species*, Chem. Commun. 1996, pp1543–1544.

J.K. MacDougall, et al., Direct formation of alcohols by hydrocarbonylation of alkenes under mild conditions using rhodium trialkylphosphine catalysts.

J.K. MacDougall et al., Metal Hydroxycarbene–Like Intermediates in the Hydrocarbonylation of Alkenese to Alcohols Catalysed by Rhodium Complexes, Polyhedron vol. 12 No. 23, pp. 2877–2881.

M.C. Simpson et al., Hydrocarbonylation of prop–2–en–1–ol to butane–1,4–diol and 2–methylpropan–1–ol catalysed by rhodium triethylphosphine complexes.

M.C. Simpson et al., "Catalytic applications of rhodium complexes containing triakylphosphines", Coordination Chemistry Reviews 155, 1996, pp.163–207.

Chem. Abs. 1972, 77, 125982t.

Chem. Abs. 1969, 71, 1, 812, 504.

*Primary Examiner*—John Kight
*Assistant Examiner*—Charanjit S. Aulakh
*Attorney, Agent, or Firm*—Gerald L. Coon

[57] ABSTRACT

This invention relates in part to processes for producing one or more substituted or unsubstituted saturated alcohols which comprise reacting one or more substituted or unsubstituted alkadienes with carbon monoxide and hydrogen in the presence of a metal-ligand complex catalyst and a promoter and optionally free ligand to produce said one or more substituted or unsubstituted saturated alcohols. The substituted and unsubstituted saturated alcohols produced by the processes of this invention can undergo further reaction(s) to afford desired derivatives thereof. This invention also relates in part to reaction mixtures containing one or more substituted or unsubstituted saturated alcohols as principal product(s) of reaction.

20 Claims, No Drawings

PROCESSES FOR PRODUCING SATURATED ALCOHOLS

This application is a continuation-in-part of copending U.S. patent application Ser. No. 08/843,381, filed Apr. 15, 1997.

BRIEF SUMMARY OF THE INVENTION

Technical Field

This invention relates in part to processes for producing one or more substituted or unsubstituted saturated alcohols, e.g., 1-pentanols, or reaction mixtures comprising one or more substituted or unsubstituted saturated alcohols. This invention also relates in part to reaction mixtures containing one or more substituted or unsubstituted saturated alcohols as the principal product(s) of reaction.

BACKGROUND OF THE INVENTION

Saturated alcohols are useful in a variety of applications, e.g. solvents and intermediates. There is a need to produce saturated alcohols in high selectivities in a manner which can suitably be employed in a commercial process. Accordingly, it would be desirable to selectively produce saturated alcohols (e.g., 1-pentanols) from a relatively inexpensive starting material (e.g., butadiene) and by a process (e.g., hydrocarbonylation) which can be employed commercially.

DISCLOSURE OF THE INVENTION

It has been discovered that alkadienes, e.g., butadiene, can be hydrocarbonylated to saturated alcohols, e.g., 1-pentanols, in high selectivities. In particular, it has been surprisingly discovered that alkadienes can be converted to linear saturated alcohols in high normal:branched isomer ratios, e.g., butadiene hydrocarbonylated to 1-pentanols in high normal:branched isomer ratios. It has been discovered that the high selectivities and high normal:branched isomer ratios result from conducting the hydrocarbonylation in the presence of a metal-ligand complex catalyst and optionally free ligand in which the ligand is preferably an organophosphine ligand of high basicity and low steric bulk and in the presence of a promoter, i.e., an organic or inorganic compound with an ionizable hydrogen of pKa of from about 1 to about 35.

This invention relates to processes for producing one or more substituted or unsubstituted saturated alcohols which comprise subjecting one or more substituted or unsubstituted alkadienes to hydrocarbonylation in the presence of a hydrocarbonylation catalyst, e.g., metal-organophosphorus ligand complex catalyst, and a promoter and optionally free ligand to produce said one or more substituted or unsubstituted saturated alcohols. In a preferred embodiment, the hydrocarbonylation catalyst is a metal-organophosphine ligand complex catalyst and the promoter is the one or more substituted or unsubstituted saturated alcohols and optionally other products of the process.

This invention also relates to processes for producing one or more substituted or unsubstituted saturated alcohols which comprise reacting one or more substituted or unsubstituted alkadienes with carbon monoxide and hydrogen in the presence of a metal-ligand complex catalyst and a promoter and optionally free ligand to produce said one or more substituted or unsubstituted saturated alcohols. In a preferred embodiment, the metal-ligand complex catalyst is a metal-organophosphorus ligand complex catalyst and the promoter is the one or more substituted or unsubstituted saturated alcohols and optionally other products of the process.

This invention further relates to processes for producing one or more substituted or unsubstituted saturated alcohols which comprise reacting one or more substituted or unsubstituted alkadienes with carbon monoxide and hydrogen in the presence of a metal-organophosphorus ligand complex catalyst and a promoter and optionally free organophosphorus ligand to produce said one or more substituted or unsubstituted saturated alcohols. In a preferred embodiment, the metal-organophosphorus ligand complex catalyst is a metal-organophosphine ligand complex catalyst and the promoter is the one or more substituted or unsubstituted saturated alcohols and optionally other products of the process.

This invention yet further relates to processes for producing one or more substituted or unsubstituted 1-pentanols which comprise reacting one or more substituted or unsubstituted butadienes with carbon monoxide and hydrogen in the presence of a metal-organophosphorus ligand complex catalyst and a promoter and optionally free organophosphorus ligand to produce said one or more substituted or unsubstituted 1-pentanols. In a preferred embodiment, the metal-organophosphorus ligand complex catalyst is a metal-organophosphine ligand complex catalyst and the promoter is the one or more substituted or unsubstituted saturated alcohols and optionally other products of the process.

This invention also relates in part to a process for producing a batchwise or continuously generated reaction mixture comprising:

(1) one or more substituted or unsubstituted 1-pentanols;
(2) optionally one or more substituted or unsubstituted cis-2-pentenols, trans-2-pentenols, cis-3-pentenols, trans-3-pentenols and/or 4-pentenols;
(3) optionally one or more substituted or unsubstituted cis-2-pentenals, trans-2-pentenals, cis-3-pentenals, trans-3-pentenals and/or 4-pentenals;
(4) optionally one or more substituted or unsubstituted valeraldehydes;
(5) optionally one or more substituted or unsubstituted lactols, diols and/or hydroxyaldehydes, e.g., 2-methylvalerolactol, 2-ethylbutyrolactol, 2-methyl-1, 5-pentanediol, 2-ethyl-1,4-butanediol, 1,6-hexanediol and 6-hydroxyhexanal; and
(6) one or more substituted or unsubstituted butadienes, e.g., butadiene;

wherein the weight ratio of the sum of component (1) to the sum of components (2), (3), (4) and (5) is greater than about 0.1, preferably greater than about 0.25, more preferably greater than about 1.0; and the weight ratio of component (6) to the sum of components (1), (2), (3), (4) and (5) is about 0 to about 100, preferably about 0.001 to about 50; which process comprises reacting one or more substituted or unsubstituted butadienes with carbon monoxide and hydrogen in the presence of a metal-ligand complex catalyst and a promoter and optionally free ligand to produce said batchwise or continuously generated reaction mixture. In a preferred embodiment, the metal-ligand complex catalyst is a metal-organophosphine ligand complex catalyst and the promoter is the one or more substituted or unsubstituted saturated alcohols and optionally other products of the process.

This invention further relates to a process for producing a reaction mixture comprising one or more substituted or unsubstituted saturated alcohols which process comprises reacting one or more substituted or unsubstituted alkadienes with carbon monoxide and hydrogen in the presence of a metal-ligand complex catalyst and a promoter and optionally free ligand to produce said reaction mixture comprising one or more substituted or unsubstituted saturated alcohols. In a preferred embodiment, the metal-ligand complex catalyst is a metal-organophosphine ligand complex catalyst and the promoter is the one or more substituted or unsubstituted saturated alcohols and optionally other products of the process.

This invention yet further relates to a process for producing a reaction mixture comprising one or more substituted or unsubstituted 1-pentanols which process comprises reacting one or more substituted or unsubstituted butadienes with carbon monoxide and hydrogen in the presence of a metal-organophosphorus ligand complex catalyst and a promoter and optionally free organophosphorus ligand to produce said reaction mixture comprising one or more substituted or unsubstituted 1-pentanols. In a preferred embodiment, the metal-organophosphorus ligand complex catalyst is a metal-organophosphine ligand complex catalyst and the promoter is the one or more substituted or unsubstituted saturated alcohols and optionally other products of the process.

The processes of this invention can achieve high selectivities of alkadienes to saturated alcohols, e.g., selectivities of butadienes to 1-pentanols of up to 75% by weight or greater may be achieved by the processes of this invention. The processes of this invention can achieve high normal:branched isomer ratios of saturated alcohols, e.g., normal:branched isomer ratios of about 5:1 or greater, preferably about 10:1 or greater, and more preferably about 20:1 or greater may be achieved by the processes of this invention.

This invention also relates in part to a batchwise or continuously generated reaction mixture comprising:

(1) one or more substituted or unsubstituted 1-pentanols;

(2) optionally one or more substituted or unsubstituted cis-2-pentenols, trans-2-pentenols, cis-3-pentenols, trans-3-pentenols and/or 4-pentenols;

(3) optionally one or more substituted or unsubstituted cis-2-pentenals, trans-2-pentenals, cis-3-pentenals, trans-3-pentenals and/or 4-pentenals;

(4) optionally one or more substituted or unsubstituted valeraldehydes;

(5) optionally one or more substituted or unsubstituted lactols, diols and/or hydroxyaldehydes, e.g., 2-methylvalerolactol, 2-ethylbutyrolactol, 2-methyl-1,5-pentanediol, 2-ethyl-1,4-butanediol, 1,6-hexanediol and 6-hydroxyhexanal; and (6) one or more substituted or unsubstituted butadienes, e.g., butadiene;

wherein the weight ratio of the sum of component (1) to the sum of components (2), (3), (4) and (5) is greater than about 0.1, preferably greater than about 0.25, more preferably greater than about 1.0; and the weight ratio of component (6) to the sum of components (1), (2), (3), (4) and (5) is about 0 to about 100, preferably about 0.001 to about 50.

This invention further relates in part to a reaction mixture comprising one or more substituted or unsubstituted saturated alcohols in which said reaction mixture is prepared by a process which comprises reacting one or more substituted or unsubstituted alkadienes with carbon monoxide and hydrogen in the presence of a metal-ligand complex catalyst and a promoter and optionally free ligand to produce said reaction mixture comprising one or more substituted or unsubstituted saturated alcohols. In a preferred embodiment, the metal-ligand complex catalyst is a metal-organophosphine ligand complex catalyst and the promoter is the one or more substituted or unsubstituted saturated alcohols and optionally other products of the process.

This invention yet further relates in part to a reaction mixture comprising one or more substituted or unsubstituted 1-pentanols in which said reaction mixture is prepared by a process which comprises reacting one or more substituted or unsubstituted butadienes with carbon monoxide and hydrogen in the presence of a metal-organophosphorus ligand complex catalyst and a promoter and optionally free organophosphorus ligand to produce said reaction mixture comprising one or more substituted or unsubstituted 1-pentanols. In a preferred embodiment, the metal-organophosphorus ligand complex catalyst is a metal-organophosphine ligand complex catalyst and the promoter is the one or more substituted or unsubstituted saturated alcohols and optionally other products of the process.

The reaction mixtures of this invention are distinctive insofar as the processes for their preparation achieve the generation of high selectivities and high normal:branched isomer ratios of saturated alcohols, e.g., 1-pentanols, in a manner which can be suitably employed in a commercial process for the manufacture of saturated alcohols. In particular, the reaction mixtures of this invention are distinctive insofar as the processes for their preparation allow for the production of 1-pentanols in relatively high yields without generating large amounts of less desirable byproducts, e.g., one or more substituted or unsubstituted 2-methylbutan-1-ols.

DETAILED DESCRIPTION

The hydrocarbonylation processes of this invention involve converting one or more substituted or unsubstituted alkadienes to one or more substituted or unsubstituted saturated alcohols. The hydrocarbonylation processes of this invention may be conducted in one or more steps or stages, preferably a one step process. As used herein, the term "hydrocarbonylation" is contemplated to include all permissible hydrocarbonylation processes which involve converting one or more substituted or unsubstituted alkadienes to one or more substituted or unsubstituted saturated alcohols.

The hydrocarbonylation process involves the production of saturated alcohols by reacting an alkadiene with carbon monoxide and hydrogen in the presence of a metal-ligand complex catalyst and optionally free ligand in a liquid medium that also contains a promoter. The reaction may be carried out in a continuous single pass mode in a continuous gas recycle manner or more preferably in a continuous liquid catalyst recycle manner as described below. The hydrocarbonylation processing techniques employable herein may correspond to any known processing techniques.

The hydrocarbonylation process mixtures employable herein includes any solution derived from any corresponding hydrocarbonylation process that may contain at least some amount of four different main ingredients or components, i.e., the saturated alcohol product, a metal-ligand complex catalyst, a promoter and optionally free ligand, said ingredients corresponding to those employed and/or produced by the hydrocarbonylation process from whence the hydrocarbonylation process mixture starting material may be derived. By "free ligand" is meant ligand that is not complexed with (tied to or bound to) the metal, e.g., rhodium atom, of the complex catalyst. It is to be understood that the hydrocarbonylation process mixture compositions employable herein can and normally will contain minor amounts of additional ingredients such as those which have either been deliberately employed in the hydrocarbonylation process or formed in situ during said process. Examples of such ingredients that can also be present include unreacted alkadiene starting material, carbon monoxide and hydrogen gases, and in situ formed type products, such as saturated alcohols and/or unreacted isomerized olefins corresponding to the alkadiene starting materials, and high boiling liquid byproducts, as well as other inert co-solvent type materials or hydrocarbon additives, if employed.

The catalysts useful in the hydrocarbonylation process include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-organophosphorus ligand complexes and free organophosphorus ligand include mono-, di-, tri- and higher poly-(organophosphorus) compounds, preferably those of high basicity and low steric bulk. Illustrative permissible organophosphorus ligands include, for example, organophosphines, organophosphites, organophosphonites, organophosphinites, organophosphorus nitrogen-containing ligands, organophosphorus sulfur-containing ligands, organophosphorus silicon-containing ligands and the like. Other permissible ligands include, for example, heteroatom-containing ligands such as described in U.S. patent application Ser. No. 08/818,781, filed Mar. 10, 1997, the disclosure of which is incorporated herein by reference. Mixtures of such ligands may be employed if desired in the metal-ligand complex catalyst and/or free ligand and such mixtures may be the same or different. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, i.e., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $BF_4$, $PF_6$, $NO_2$, $NO_3$, $CH_3O$, $CH_2$=$CHCH_2$, $CH_3CH$=$CHCH_2$, $C_6H_5CN$, $CH_3CN$, NO, $NH_3$, pyridine, $(C_2H_5)_3N$, monoolefins, diolefins and triolefins, tetrahydrofuran, and the like. It is of course to be understood that the complex species are preferably free of any additional organic ligand or anion that might poison the catalyst and have an undue adverse effect on catalyst performance. It is preferred in the metal-ligand complex catalyzed hydrocarbonylation processes that the active catalysts be free of halogen and sulfur directly bonded to the metal, although such may not be absolutely necessary. Preferred metal-ligand complex catalysts include rhodium-organophosphine ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per metal, e.g., rhodium. As noted above, it is considered that the catalytic species of the preferred catalyst employed in the hydrocarbonylation process may be complexed with carbon monoxide and hydrogen in addition to the organophosphorus ligands in view of the carbon monoxide and hydrogen gas employed by the hydrocarbonylation process.

Among the organophosphines that may serve as the ligand of the metal-organophosphine complex catalyst and/or free organophosphine ligand of the hydrocarbonylation process mixture starting materials are mono-, di-, tri- and poly-(organophosphines) such as triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl diphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substituent that does not unduly adversely affect the desired result of the hydrocarbonylation process. The organophosphine ligands employable in the hydrocarbonylation process and/or methods for their preparation are known in the art.

Illustrative triorganophosphine ligands may be represented by the formula:

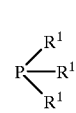

(I)

wherein each $R^1$ is the same or different and is a substituted or unsubstituted monovalent hydrocarbon radical, e.g., an alkyl, cycloalkyl or aryl radical. In a preferred embodiment, each $R^1$ is the same or different and is selected from primary alkyl, secondary alkyl, tertiary alkyl and aryl. Suitable hydrocarbon radicals may contain from 1 to 24 carbon atoms or greater. Illustrative substituent groups that may be present on the hydrocarbon radicals include, e.g., substituted or unsubstituted alkyl radicals, substituted or unsubstituted alkoxy radicals, substituted or unsubstituted silyl radicals such as —$Si(R^2)_3$; amino radicals such as —$N(R^2)_2$; acyl radicals such as —$C(O)R^2$; carboxy radicals such as —$C(O)OR^2$; acyloxy radicals such as —$OC(O)R^2$; amido radicals such as —$C(O)N(R^2)_2$ and —$N(R^2)C(O)R^2$; ionic radicals such as —SO₃M wherein M represents inorganic or organic cationic atoms or radicals; sulfonyl radicals such as —SO₂R²; ether radicals such as —OR²; sulfinyl radicals such as —SOR²; selenyl radicals such as —SeR²; sulfenyl radicals such as —SR² as well as halogen, nitro, cyano, trifluoromethyl and hydroxy radicals, and the like, wherein each R² individually represents the same or different substituted or unsubstituted monovalent hydrocarbon radical, with the proviso that in amino substituents such as —N(R²)₂, each R² taken together can also represent a divalent bridging group that forms a heterocyclic radical with the nitrogen atom and in amido substituents such as C(O)N(R²)₂ and —N(R²)C(O)R² each —R² bonded to N can also be hydrogen. Illustrative alkyl radicals include, e.g., methyl, ethyl, propyl, butyl, octyl, cyclohexyl, isopropyl and the like. Illustrative aryl radicals include, e.g., phenyl, naphthyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, 4-dimethylaminophenyl, 2,4,6-trimethoxyphenyl and the like.

Illustrative specific organophosphines include, e.g., trimethylphosphine, triethylphosphine, tributylphosphine, trioctylphosphine, diethylbutylphosphine, diethyl-n-propylphosphine, diethylisopropylphosphine, diethylbenzylphosphine, diethylcyclopentylphosphine, diethylcyclohexylphosphine, triphenylphosphine, tris-p-tolylphosphine, tris-p-methoxyphenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, DIOP, i.e., (4R,5R)-(−)-O-isopropylidene-2,3-dihydroxy-1,4-bis(diphenylphosphino)butane and/or (4S,5S)-(+)-O-isopropylidene-2,3-dihydroxy-1,4-bis(diphenylphosphino)butane and/or (4S,5R)-(−)-O-isopropylidene-2,3-dihydroxy-1,4-bis(diphenylphosphino)butane, substituted or unsubstituted bicyclic bisphosphines such as 1,2-bis(1,4-cyclooctylenephosphino)ethane, 1,3-bis(1,4-cyclooctylenephosphino)propane, 1,3-bis(1,5-cyclooctylenephosphino)propane and 1,2-bis(2,6-dimethyl-1,4-cyclooctylenephosphino)ethane, substituted or unsubstituted bis(2,2'-diphenylphosphinomethyl)biphenyl such as bis(2,2'-diphenylphosphinomethyl)biphenyl and bis{2,2'-di(4-fluorophenyl)phosphinomethyl}biphenyl, MeC(CH₂PPh₂)₃ (triphos), NaO₃S(C₆H₄)CH₂C(CH₂PPh₂)₃ (sulphos), bis(diphenylphosphino)ferrocene, bis(diisopropylphosphino)ferrocene, bis(diphenylphosphino)ruthenocene, as well as the alkali and alkaline earth metal salts of sulfonated triphenylphosphines, e.g., of (tri-m-sulfophenyl)phosphine and of (m-sulfophenyl)diphenylphosphine and the like.

The preferred organophosphorus ligands which make up the metal-organophosphorus ligand complex catalysts and free organophosphorus ligands are high basicity ligands. In general, the basicity of the organophosphorus ligands should be greater than or equal to the basicity of triphenylphosphine (pKb of 2.74), e.g., from about 2.74 to about 15. Suitable organophosphorus ligands have a pKb of about 3 or greater, preferably a pKb of about 3 to about 12, and more preferably a pKb of about 5 to about 12. pKb values for illustrative organophosphorus ligands useful in this invention are given in the Table I below. In addition, the organophosphorus ligands useful in this invention have a steric bulk sufficient to promote the hydrocarbonylation reaction. The steric bulk of monodentate organophosphorus ligands should be lower than or equal to a Tolman cone angle of 210°, preferably lower than or equal to the steric bulk of tricyclohexylphosphine (Tolman cone angle=170°). Organophosphorus ligands having desired basicity and steric bulk include, for example, substituted or unsubstituted tri-primary-alkylphosphines (e.g., trioctylphosphine, diethylbutylphosphine, diethylisobutylphosphine), di-primary-alkylarylphosphines (e.g., diethylphenylphosphine, diethyl-p-N,N-dimethylphenylphosphine), di-primary-alkyl-mono-secondary-alkylphosphines (e.g., diethylisopropylphosphine, diethylcyclohexylphosphine), di-primary-alkyl-tert-alkylphosphines (e.g., diethyl-tert-butylphosphine), mono-primary-alkyl-diarylphosphines (e.g., diphenylmethylphosphine), mono-primary-alkyl-di-secondary-alkylphosphines (e.g., dicyclohexylethylphosphine), triarylphosphines (e.g., tri-para-N,N-dimethylaminophenylphosphine), tri-secondarylalkylphosphines (e.g., tricyclohexylphosphine), mono-primaryalkyl-mono-secondaryalkyl-mono-tertiary alkylphosphines (e.g., ethylisopropyltert-butylphosphine) and the like. The permissible organophosphorus ligands may be substituted with any suitable functionalities and may include the promoter as described hereinbelow.

TABLE I

| Organophosphorus Ligand | pKb |
|---|---|
| Trimethylphosphine | 8.7 |
| Triethylphosphine | 8.7 |
| Tri-n-propylphosphine | 8.7 |
| Tri-n-butylphosphine | 8.4 |
| Tri-n-octylphosphine | 8.4 |
| Tri-tert-butylphosphine | 11.4 |
| Diethyl-tert-butylphosphine | 10.1 |
| Tricyclohexylphosphine | 10 |
| Diphenylmethylphosphine | 4.5 |
| Diethylphenylphosphine | 6.4 |
| Diphenylcyclohexylphosphine | 5 |
| Diphenylethylphosphine | 4.9 |
| Tri(p-methoxyphenyl)phosphine | 4.6 |
| Triphenylphosphine | 2.74 |
| Tri(p-N,N-dimethylaminophenyl)phosphine | 8.65 |
| Tri(p-methylphenyl)phosphine | 3.84 |

More particularly, illustrative metal-organophosphine complex catalysts and illustrative free organophosphine ligands include, for example, those disclosed in U.S. Pat. Nos. 3,239,566, 3,527,809; 4,148,830; 4,247,486; 4,283,562; 4,400,548; 4,482,749 and 4,861,918, the disclosures of which are incorporated herein by reference.

Other illustrative permissible organophosphorus ligands which may make up the metal-organophosphorus ligand complexes and free organophosphorus ligands include, for example, those disclosed in U.S. Pat. Nos. 4,567,306, 4,599,206, 4,668,651, 4,717,775, 3,415,906, 4,567,306, 4,599,206, 4,748,261, 4,769,498, 4,717,775, 4,885,401, 5,202,297, 5,235,113, 5,254,741, 5,264,616, 5,312,996, 5,364,950, 5,391,801, U.S. patent application Ser. No. 08/753,505, filed Nov. 26, 1996, and U.S. patent application Ser. No. 08/843,389, filed Apr. 15, 1997, the disclosures of which are incorporated herein by reference.

The metal-ligand complex catalysts employable in this invention may be formed by methods known in the art. The metal-ligand complex catalysts may be in homogeneous or heterogeneous form. For instance, preformed metal hydrido-carbonyl-organophosphorus ligand catalysts may be prepared and introduced into the reaction mixture of a hydrocarbonylation process. More preferably, the metal-ligand complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a promoter with the organophosphine ligand to form a catalytic rhodium-organophosphine ligand complex precursor which is introduced into the reactor along with excess free organophosphine ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydrocarbonylation process.

More particularly, a catalyst precursor composition can be formed consisting essentially of a solubilized metal-ligand complex precursor catalyst, a promoter and free ligand. Such precursor compositions may be prepared by forming a solution of a metal starting material, such as a metal oxide, hydride, carbonyl or salt, e.g. a nitrate, which may or may not be in complex combination with a ligand as defined herein. Any suitable metal starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial metal, may be complexed to the metal either prior to or in situ during the hydrocarbonylation process.

By way of illustration, the preferred catalyst precursor composition of this invention consists essentially of a solubilized rhodium carbonyl organophosphine ligand complex precursor catalyst, a promoter and free organophosphine ligand prepared by forming a solution of rhodium dicarbonyl acetylacetonate, a promoter and an organophosphine ligand as defined herein. The organophosphine ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphine ligand complex precursor are soluble can be employed. The amounts of rhodium complex catalyst precursor, organic solvent and organophosphine ligand, as well as their preferred embodiments present in such catalyst precursor compositions may obviously correspond to those amounts employable in the hydrocarbonylation process of this invention. Experience has shown that the acetylacetonate ligand of the precursor catalyst is replaced after the hydrocarbonylation process has begun with a different ligand, e.g., hydrogen, carbon monoxide or organophosphine ligand, to form the active complex catalyst as explained above. In a continuous process, the acetylacetone which is freed from the precursor catalyst under hydrocarbonylation conditions is removed from the reaction medium with the product alcohol and thus is in no way detrimental to the hydrocarbonylation process. The use of such preferred rhodium complex catalytic precursor compositions provides a simple economical and efficient method for handling the rhodium precursor metal and hydrocarbonylation start-up.

Accordingly, the metal-ligand complex catalysts used in the process of this invention consists essentially of the metal complexed with carbon monoxide and a ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphine ligand complex catalyst may be present as a result of being ligands bound to a precursor catalyst and/or as a result of in situ formation, e.g., due to the hydrogen and carbon monoxide gases employed in hydrocarbonylation process of this invention.

As noted the hydrocarbonylation process involves the use of a metal-ligand complex catalyst as described herein. Of course mixtures of such catalysts can also be employed if desired. The amount of metal-ligand complex catalyst present in the reaction medium of a given hydrocarbonylation process need only be that minimum amount necessary to provide the given metal concentration desired to be employed and which will furnish the basis for at least the catalytic amount of metal necessary to catalyze the particular hydrocarbonylation process involved such as disclosed, for example, in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydrocarbonylation process conditions and solvent employed.

In general, the organophosphorus ligand concentration in hydrocarbonylation process mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydrocarbonylation process mixtures may be as high as about 2000 parts per million by weight or greater based on the weight of the reaction mixture. Preferably the metal concentration is between about 50 and 1500 parts per million by weight based on the weight of the reaction mixture, and more preferably is between about 70 and 1200 parts per million by weight based on the weight of the reaction mixture.

In addition to the metal-ligand complex catalyst, free ligand (i.e., ligand that is not complexed with the rhodium metal) may also be present in the hydrocarbonylation process medium. The free ligand may correspond to any of the above-defined ligands discussed above as employable herein. It is preferred that the free ligand be the same as the ligand of the metal-ligand complex catalyst employed. However, such ligands need not be the same in any given process. The hydrocarbonylation process may involve up to 100 moles, or higher, of free ligand per mole of metal in the hydrocarbonylation process medium. Preferably the hydrocarbonylation process is carried out in the presence of from about 1 to about 50 moles of coordinatable phosphorus, more preferably from about 1 to about 20 moles of coordinatable phosphorus, and most preferably from about 1 to about 8 moles of coordinatable phosphorus, per mole of metal present in the reaction medium; said amounts of coordinatable phosphorus being the sum of both the amount of coordinatable phosphorus that is bound (complexed) to the rhodium metal present and the amount of free (non-complexed) coordinatable phosphorus present. Of course, if desired, make-up or additional coordinatable phosphorus can be supplied to the reaction medium of the hydrocarbonylation process at any time and in any suitable manner, e.g. to maintain a predetermined level of free ligand in the reaction medium.

As indicated above, the hydrocarbonylation catalyst may be in heterogeneous form during the reaction and/or during the product separation. Such catalysts are particularly advantageous in the hydrocarbonylation of alkadienes to produce high boiling or thermally sensitive alcohols, so that the catalyst may be separated from the products by filtration or decantation at low temperatures. For example, the rhodium catalyst may be attached to a support so that the catalyst retains its solid form during both the hydrocarbonylation and separation stages, or is soluble in a liquid reaction medium at high temperatures and then is precipitated on cooling.

As an illustration, the rhodium catalyst may be impregnated onto any solid support, such as inorganic oxides, (e.g., alumina, silica, titania, or zirconia) carbon, or ion exchange resins. The catalyst may be supported on, or intercalated inside the pores of, a zeolite or glass; the catalyst may also be dissolved in a liquid film coating the pores of said zeolite or glass. Such zeolite-supported catalysts are particularly advantageous for producing one or more regioisomeric alcohols in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The rhodium catalyst may be attached to a thin film or membrane support, such as cellulose acetate or polyphenylenesulfone, as described in for example J. Mol. Cat. 1990, 63, 213–221.

The rhodium catalyst may be attached to an insoluble polymeric support through an organophosphorus-containing ligand, such as a phosphine or phosphite, incorporated into the polymer. Such polymer-supported ligands are well known, and include such commercially available species as the divinylbenzene/polystyrene-supported triphenylphosphine. The supported ligand is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire hydrocarbonylation and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

When the rhodium catalyst is in a heterogeneous or supported form, the reaction may be carried out in the gas phase. More preferably, the reaction is carried out in the slurry phase due to the high boiling points of the products, and to avoid decomposition of the product alcohols. The catalyst may then be separated from the product mixture by filtration or decantation.

The processes of this invention can be operated over a wide range of reaction rates (m/L/h=moles of product/liter of reaction solution/hour). Typically, the reaction rates are at least 0.01 m/L/h or higher, preferably at least 0.1 m/L/h or higher, and more preferably at least 0.3 m/L/h or higher. Higher reaction rates are generally preferred from an economic standpoint, e.g., smaller reactor size, etc.

The substituted and unsubstituted alkadiene starting materials useful in the hydrocarbonylation processes include, but are not limited to, conjugated aliphatic diolefins represented by the formula:

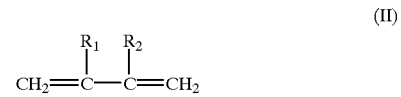

(II)

wherein $R_1$ and $R_2$ are the same or different and are hydrogen, halogen or a substituted or unsubstituted hydrocarbon radical. The alkadienes can be linear or branched and can contain substituents (e.g., alkyl groups, halogen atoms, amino groups or silyl groups). Illustrative of suitable alkadiene starting materials are butadiene, isoprene, dimethyl butadiene, cyclopentadiene and chloroprene. Most preferably, the alkadiene starting material is butadiene itself ($CH_2$=CH—CH=$CH_2$). For purposes of this invention, the term "alkadiene" is contemplated to include all permissible substituted and unsubstituted conjugated diolefins, including all permissible mixtures comprising one or more substituted and unsubstituted conjugated diolefins. Illustrative of suitable substituted and unsubstituted alkadienes (including derivatives of alkadienes) include those permissible substituted and unsubstituted alkadienes described in Kirk-Othmer, Encyclopedia of Chemical Technology, Fourth Edition, 1996, the pertinent portions of which are incorporated herein by reference.

The particular hydrocarbonylation reaction conditions are not narrowly critical and can be any effective hydrocarbonylation procedures sufficient to produce one or more saturated alcohols. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions. The hydrocarbonylation process conditions may include any suitable type hydrocarbonylation conditions heretofore employed for producing alcohols. The total pressure employed in the hydrocarbonylation process may range in general from about 1 to about 10,000 psia, preferably from about 20 to 3000 psia and more preferably from about 50 to about 2000 psia. The total pressure of the hydrocarbonylation process will be dependent on the particular catalyst system employed.

More specifically, the carbon monoxide partial pressure of the hydrocarbonylation process in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed. It is understood that carbon monoxide and hydrogen can be employed separately, either alone or in mixture with each other, i.e., synthesis gas, or may be produced in situ under reaction conditions and/or be derived from the promoter or solvent (not necessarily involving free hydrogen or carbon monoxide). In an embodiment, the hydrogen partial pressure and carbon monoxide partial pressure are sufficient to prevent or minimize derivatization, e.g., further hydrocarbonylation of penten-1-ols.

In conducting the process of this invention, it may be desirable to maintain some alkadiene partial pressure or when the alkadiene conversion is complete, the carbon monoxide and hydrogen partial pressures should be sufficient to prevent or minimize derivatization, e.g., further hydrocarbonylation of penten-1-ols. The alkadiene partial pressure of the hydrocarbonylation process may vary over a wide range. For example, the alkadiene, e.g., butadiene, hydrocarbonylation may be conducted at an alkadiene partial pressure of greater than 0 psi, if desired greater than 5 psi.

Further, the hydrocarbonylation process may be conducted at a reaction temperature from about 20° C. to about 200° C., preferably from about 50° C. to about 150° C., and more preferably from about 65° C. to about 115° C. The temperature must be sufficient for reaction to occur (which may vary with catalyst system employed), but not so high that ligand or catalyst decomposition occurs.

The hydrocarbonylation process may be conducted at a residence time of from about 10 minutes or less to about 10 hours or longer, preferably from about 30 minutes to about 8 hours, and more preferably from about 90 minutes to about 4 hours. The residence time must be sufficient for reaction to occur (which may vary with catalyst system employed), but not so long that ligand or catalyst decomposition occurs.

Of course, it is to be also understood that the hydrocarbonylation process conditions employed will be governed by the type of saturated alcohol product desired.

The hydrocarbonylation process is also conducted in the presence of a promoter. As used herein, "promoter" means an organic or inorganic compound with an ionizable hydrogen of pKa of from about 1 to about 35. Illustrative promoters include, for example, protic solvents, organic and inorganic acids, alcohols, water, phenols, thiols, thiophenols, nitroalkanes, ketones, nitriles, amines (e.g., pyrroles and diphenylamine), amides (e.g., acetamide), mono-, di- and trialkylammonium salts, and the like. Approximate pKa values for illustrative promoters useful in this invention are given in the Table II below. The promoter may be present in the hydrocarbonylation reaction mixture either alone or incorporated into the ligand structure, either as the metal-ligand complex catalyst or as free ligand, or into the alkadiene structure. The desired promoter will depend on the nature of the ligands and metal of the metal-ligand complex catalysts. In general, a catalyst with a more basic metal-bound acyl or other intermediate will require a lower concentration and/or a less acidic promoter.

Although it is not intended herein to be bound to any theory or mechanistic discourse, it appears that the promoter may function to transfer a hydrogen ion to or otherwise activate a catalyst-bound acyl or other intermediate. Mixtures of promoters in any permissible combination may be useful in this invention. A preferred class of promoters includes those that undergo hydrogen bonding, e.g., NH, OH and SH-containing groups and Lewis acids, since this is believed to facilitate hydrogen ion transfer to or activation of the metal-bound acyl or other intermediate. In general, the amount of promoter may range from about 10 parts per million or so up to about 99 percent by weight or more based on the total weight of the hydrocarbonylation process mixture starting materials.

TABLE II

| Promoter | pKa |
|---|---|
| ROH (R = alkyl) | 15–19 |
| ROH (R = aryl) | 8–11 |
| RCONHR (R = hydrogen or alkyl, e.g., acetamide) | 15–19 |
| $R_3NH^+$, $R_2NH_2^+$ (R = alkyl) | 10–11 |
| $RCH_2NO_2$ | 8–11 |
| $RCOCH_2R$ (R = alkyl) | 19–20 |
| RSH (R = alkyl) | 10–11 |
| RSH (R = aryl) | 8–11 |
| $CNCH_2CN$ | 11 |
| Diarylamine | 21–24 |
| Pyrrole | 20 |
| Pyrrolidine | 34 |

The concentration of the promoter employed will depend upon the details of the catalyst system employed. Without wishing to be bound by theory, the promoter component must be sufficiently acidic and in sufficient concentration to transfer a hydrogen ion to or otherwise activate the catalyst-bound acyl or other intermediate. It is believed that a promoter component acidity or concentration which is insufficient to transfer a hydrogen ion to or otherwise activate the catalyst-bound acyl or other intermediate will result in the formation of pentenal products, rather than the preferred 1-pentanol products. The ability of a promoter component to transfer a hydrogen ion to or otherwise activate the catalyst-bound acyl or other intermediate may be governed by several factors, for example, the concentration of the promoter component, the intrinsic acidity of the promoter component (the pKa), the composition of the reaction medium (e.g., the reaction solvent) and the temperature. Promoters are chosen on the basis of their ability to transfer a hydrogen ion to or otherwise activate such a catalyst-bound acyl or other intermediate under reaction conditions sufficient to result in the formation of alcohol products, but not so high as to result in detrimental side reactions of the catalyst, reactants or products. In cases where the promoter component acidity or concentration is insufficient to do so, aldehyde products (e.g., pentenals) are initially formed which may or may not be subsequently converted to saturated alcohols, e.g., 1-pentanols.

In general, a less basic metal-bound acyl will require a higher concentration of the promoter component or a more acidic promoter component to protonate or otherwise activate it fully, such that the products are more desired 1-pentanols, rather than pentenals. This can be achieved by appropriate choice of promoter component. For example, an enabling concentration of protonated or otherwise activated catalyst-bound acyl or other intermediate can be achieved though the use of a large concentration of a mildly acidic promoter component, or through the use of a smaller concentration of a more acidic component. The promoter component is selected based upon its ability to produce the desired concentration of protonated or otherwise activated catalyst-bound acyl or other intermediate in the reaction medium under reaction conditions. In general, the intrinsic strength of an acidic material is generally defined in aqueous solution as the pKa, and not in reaction media commonly employed in hydrocarbonylation. The choice of the promoter and its concentration is made based in part upon the theoretical or equivalent pH that the promoter alone at such concentration gives in aqueous solution at 22° C. The desired theoretical or equivalent pH of promoter component solutions should be greater than 0, preferably from about 1–12, more preferably from about 2–10 and most preferably from 4–8. The theoretical or equivalent pH can be readily calculated from values of pKa's at the appropriate promoter component concentration by reference to standard tables such as those found in "Ionization Constants of Organic Acids in Aqueous Solution" (IUPAC Chemical Data Series—No. 23) by E. P Serjeant and Boyd Dempsey, Pergamon Press (1979) and "Dissociation Constants of Inorganic Acids and Bases in Aqueous Solution" (IUPAC Chemical Data Series—No. 19, by D. D. Perrin, Pergamon Press.

Depending on the particular catalyst and reactants employed, suitable promoters preferably include solvents, for example, alcohols (e.g., the saturated alcohol products such as 1-pentanols), thiols, thiophenols, selenols, tellurols, alkenes, alkynes, aldehydes, higher boiling byproducts, ketones, esters, amides, primary and secondary amines, alkylaromatics and the like. Any suitable promoter which does not unduly adversely interfere with the intended hydrocarbonylation process can be employed. Permissible protic solvents have a pKa of about 1–35, preferably a pKa of about 3–30, and more preferably a pKa of about 5–25. Mixtures of one or more different solvents may be employed if desired.

In general, with regard to the production of saturated alcohols, it is preferred to employ saturated alcohol promoters corresponding to the saturated alcohol products desired to be produced and/or higher boiling byproducts as the main protic solvents. Such byproducts can also be preformed if desired and used accordingly. Illustrative preferred protic solvents employable in the production of saturated alcohols, e.g., 1-pentanols, include alcohols (e.g., pentenols, octanols, hexanediols), amines, thiols, thiophenols, ketones (e.g. acetone and methylethyl ketone), hydroxyaldehydes (e.g., 6-hydroxyaldehyde), lactols (e.g., 2-methylvalerolactol), esters (e.g. ethyl acetate), hydrocarbons (e.g. diphenylmethane, triphenylmethane), nitrohydrocarbons (e.g. nitromethane), 1,4-butanediols and sulfolane. Suitable protic solvents are disclosed in U.S. Pat. No. 5,312,996.

As indicated above, the promoter may be incorporated into the ligand structure, either as the metal-ligand complex catalyst or as free ligand. Suitable organophosphorus ligand promoters which may be useful in this invention include, for example, tris(2-hydroxyethyl)phosphine, tris(3-hydroxypropyl)phosphine, tris(2-hydroxyphenylphosphine), tris(4-hydroxyphenylphosphine), tris(3-carboxypropyl)phosphine, tris(3-carboxamidopropyl)phosphine, diphenyl(2-hydroxyphenyl)phosphine, diethyl(2-anilinophenyl) phosphine, and tris(3-pyrroyl)phosphine. The use of ligand promoters may by particularly beneficial in those instances when the saturated alcohol product is not effective as a promoter. As with the organophosphorus ligands which make up the metal-organophosphorus ligand complex catalysts and free organophosphorus ligands, the organophosphorus ligand promoters preferably are high basicity ligands having a steric bulk lower than or equal to a Tolman cone angle of 210°, preferably lower than or equal to the steric bulk of tricyclohexylphosphine (Tolman cone angle=170°). Indeed, the organophosphorus ligand promoters may be employed as organophosphorus ligands which make up the metal-organophosphorus ligand complex catalysts and free organophosphorus ligands. Mixtures of promoters comprising one or more organophosphorus ligand promoters and mixtures comprising one or more organophosphorus ligand promoters and one or more other promoters, e.g., protic solvents, may be useful in this invention.

In an embodiment of the invention, the hydrocarbonylation process mixture may consist of one or more liquid phases, e.g. a polar and a nonpolar phase. Such processes are often advantageous in, for example, separating products from catalyst and/or reactants by partitioning into either phase. In addition, product selectivities dependent upon solvent properties may be increased by carrying out the reaction in that solvent. An application of this technology is the aqueous-phase hydrocarbonylation of alkadienes employing sulfonated phosphine ligands, hydroxylated phosphine ligands and aminated phosphine ligands for the rhodium catalyst. A process carried out in aqueous solvent is particularly advantageous for the preparation of alcohols because the products may be separated from the catalyst by extraction into a solvent.

As described herein, the phosphorus-containing ligand for the rhodium hydrocarbonylation catalyst may contain any of a number of substituents, such as cationic or anionic substituents, which will render the catalyst soluble in a polar phase, e.g. water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by for example addition of a second solvent to separate the products from the catalyst. See, for example, U.S. Pat. No. 5,180,854, the disclosure of which is incorporated herein by reference.

In an embodiment of the process of this invention, an olefin can be hydrocarbonylated along with an alkadiene using the above-described metal-ligand complex catalysts. In such cases, an alcohol derivative of the olefin is also produced along with the saturated alcohols, e.g., 1-pentanols.

Mixtures of different olefinic starting materials can be employed, if desired, in the hydrocarbonylation processes. More preferably the hydrocarbonylation process is especially useful for the production of saturated alcohols, by hydroformylating alkadienes in the presence of alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial alpha olefins containing four or more carbon atoms may contain minor amounts of corresponding internal olefins and/or their corresponding saturated hydrocarbon and that such commercial olefins need not necessarily be purified from same prior to being hydroformylated.

Illustrative of other olefinic starting materials include alpha-olefins, internal olefins, 1,3-dienes, 1,2-dienes, alkyl alkenoates, alkenyl alkanoates, alkenyl alkyl ethers, alkenols, alkenals, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, vinyl cyclohexene, allyl ethyl ether, methyl pentenoate, n-propyl-7-octenoate, pentenals, e.g., 2-pentenal, 3-pentenal and 4-pentenal; 1-pentanols, e.g., 2-1-pentanol, 3-1-pentanol and 4-1-pentanol; 3-butenenitrile, 3-pentenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta-pinene, dicyclopentadiene, cyclooctadiene, camphene, linalool, and the like. Other illustrative olefinic compounds may include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described in U.S. Pat. No. 4,329,507, the disclosure of which is incorporated herein by reference.

In those instances where the promoter is not the solvent, the hydrocarbonylation processes encompassed by this invention are conducted in the presence of an organic solvent for the metal ligand complex catalyst and free ligand. The solvent may also contain dissolved water up to the saturation limit. Depending on the particular catalyst and reactants employed, suitable organic solvents include, for example, alcohols, alkanes, alkenes, alkynes, ethers, aldehydes, higher boiling hydrocarbonylation byproducts, ketones, esters, amides, tertiary amines, aromatics and the like. Any suitable solvent which does not unduly adversely interfere with the intended hydrocarbonylation reaction can be employed. Mixtures of one or more different solvents may be employed if desired. Illustrative preferred solvents employable in the production of alcohols include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and sulfolane. Suitable solvents are disclosed in U.S. Pat. No. 5,312,996. The amount of solvent employed is not critical to the subject invention and need only be that amount sufficient to solubilize the catalyst and free ligand of the hydrocarbonylation reaction mixture to be treated. In general, the amount of solvent may range from about 5 percent by weight up to about 99 percent by weight or more based on the total weight of the hydrocarbonylation reaction mixture starting material.

Illustrative substituted and unsubstituted saturated alcohols that can be prepared by the processes of this invention include one or more of the following: alkanols such as 1-pentanols, 1-hexanols, including mixtures comprising one or more of the above saturated alcohols. Illustrative of suitable substituted and unsubstituted saturated alcohols (including derivatives of saturated alcohols) include those permissible substituted and unsubstituted saturated alcohols which are described in Kirk-Othmer, Encyclopedia of Chemical Technology, Fourth Edition, 1996, the pertinent portions of which are incorporated herein by reference.

As indicated above, it is generally preferred to carry out the hydrocarbonylation process of this invention in a continuous manner. In general, continuous hydrocarbonylation processes may involve: (a) hydrocarbonylating the alkadiene starting material(s) with carbon monoxide and hydrogen in a liquid homogeneous reaction mixture comprising a solvent, the metal-ligand complex catalyst, and free ligand; (b) maintaining reaction temperature and pressure conditions favorable to the hydrocarbonylation of the alkadiene starting material(s); (c) supplying make-up quantities of the alkadiene starting material(s), carbon monoxide and hydrogen to the reaction medium as those reactants are used up; and (d) recovering the desired alcohol hydrocarbonylation product(s) in any manner desired. The continuous reaction can be carried out in a single pass mode, i.e., wherein a vaporous mixture comprising unreacted alkadiene starting material(s) and vaporized alcohol product is removed from the liquid reaction mixture from whence the alcohol product is recovered and make-up alkadiene starting material(s), carbon monoxide and hydrogen are supplied to the liquid reaction medium for the next single pass through without recycling the unreacted alkadiene starting material(s). However, it is generally desirable to employ a continuous reaction that involves either a liquid and/or gas recycle procedure. Such types of recycle procedure are known in the art and may involve the liquid recycling of the metal-ligand complex catalyst solution separated from the desired alcohol reaction product(s).

As indicated above, the hydrocarbonylation process may involve a liquid catalyst recycle procedure. Such liquid catalyst recycle procedures are known in the art. For instance, in such liquid catalyst recycle procedures it is commonplace to continuously or intermittently remove a portion of the liquid reaction product medium, containing, e.g., the alcohol product, the solubilized metal-ligand complex catalyst, free ligand, and organic solvent, as well as byproducts produced in situ by the hydrocarbonylation and unreacted alkadiene starting material, carbon monoxide and hydrogen (syn gas) dissolved in said medium, from the hydrocarbonylation reactor, to a distillation zone, e.g., a vaporizer/separator wherein the desired alcohol product is distilled in one or more stages under normal, reduced or elevated pressure, as appropriate, and separated from the liquid medium. The vaporized or distilled desired alcohol product so separated may then be condensed and recovered in any conventional manner as discussed above. The remaining non-volatilized liquid residue which contains metal-ligand complex catalyst, solvent, free ligand and usually some undistilled alcohol product is then recycled back, with or with out further treatment as desired, along with whatever by-product and non-volatilized gaseous reactants that might still also be dissolved in said recycled liquid residue, in any conventional manner desired, to the hydrocarbonylation reactor, such as disclosed e.g., in the above-mentioned patents. Moreover the reactant gases so removed by such distillation from the vaporizer may also be recycled back to the reactor if desired.

Recovery and purification of saturated alcohols may be by any appropriate means, and may include distillation, phase separation, extraction, precipitation, absorption, crystallization, membrane separation, derivative formation and other suitable means. For example, a crude reaction product can be subjected to a distillation-separation at atmospheric or reduced pressure through a packed distillation column. Reactive distillation may be useful in conducting the hydrocarbonylation reaction.

As indicated above, at the conclusion of (or during) the hydrocarbonylation process, the desired saturated alcohols, e.g., 1-pentanols, may be recovered from the reaction mixtures used in the process of this invention. For instance, in a continuous liquid catalyst recycle reaction the portion of the liquid reaction mixture (containing 1-pentanol product, catalyst, etc.) removed from the reactor can be passed to a vaporizer/separator wherein the desired alcohol product can be separated via distillation, in one or more stages, under normal, reduced or elevated pressure, from the liquid reaction solution, condensed and collected in a product receiver, and further purified if desired. The remaining nonvolatilized catalyst containing liquid reaction mixture may then be recycled back to the reactor as may, if desired, any other volatile materials, e.g., unreacted alkadiene, together with any hydrogen and carbon monoxide dissolved in the liquid reaction after separation thereof from the condensed 1-pentanol product, e.g., by distillation in any conventional manner. It is generally desirable to employ an organophosphorus ligand whose molecular weight exceeds that of the higher boiling alcohol oligomer byproduct corresponding to the 1-pentanols being produced in the hydrocarbonylation process. Another suitable recovery technique is solvent extraction or crystallization. In general, it is preferred to separate the desired saturated alcohols from the catalyst-containing reaction mixture under reduced pressure and at low temperatures so as to avoid possible degradation of the organophosphorus ligand and reaction products. When an alpha-mono-olefin reactant is also employed, the alcohol derivative thereof can also be separated by the above methods.

More particularly, distillation and separation of the desired alcohol product from the metal-ligand complex catalyst containing product solution may take place at any suitable temperature desired. In general, it is recommended that such distillation take place at relatively low temperatures, such as below 150° C., and more preferably at a temperature in the range of from about 50° C. to about 130° C. It is also generally recommended that such alcohol distillation take place under reduced pressure, e.g., a total gas pressure that is substantially lower than the total gas pressure employed during hydrocarbonylation when low boiling alcohols (e.g., $C_5$ and $C_6$) are involved or under vacuum when high boiling alcohols (e.g. $C_7$ or greater) are involved. For instance, a common practice is to subject the liquid reaction product medium removed from the hydrocarbonylation reactor to a pressure reduction so as to volatilize a substantial portion of the unreacted gases dissolved in the liquid medium which now contains a much lower synthesis gas concentration than was present in the hydrocarbonylation process medium to the distillation zone, e.g. vaporizer/separator, wherein the desired alcohol product is distilled. In general, distillation pressures ranging from vacuum pressures on up to total gas pressure of about 50 psig should be sufficient for most purposes.

While not wishing to be bound to any particular reaction mechanism, it is believed that the overall hydrocarbonylation reaction generally proceeds in one step, i.e., the one or more substituted or unsubstituted alkadienes (e.g., butadiene) are converted to one or more substituted or unsubstituted saturated alcohols (e.g., 1-pentanol) either directly or through one or more intermediates (e.g., a 3-pentenal/ol and/or 4-pentenal/ol). This invention is not intended to be limited in any manner by any particular reaction mechanism, but rather encompasses all permissible reaction mechanisms involved in hydrocarbonylating one or more substituted or unsubstituted alkadienes with carbon monoxide and hydrogen in the presence of a metal-ligand complex catalyst and a promoter and optionally free ligand to produce one or more substituted or unsubstituted saturated alcohols.

The saturated alcohol products have a wide range of utilities that are well known in the art, e.g., they are useful as starting materials/intermediates in chemical syntheses.

A process involving the hydrocarbonylation of one or more substituted or unsubstituted alkadienes to produce one or more substituted or unsubstituted unsaturated alcohols is disclosed in copending U.S. patent application Ser. No. 08/843,381, filed Apr. 15, 1997, the disclosure of which is incorporated herein by reference. A process involving the reductive hydroformylation of one or more substituted or unsubstituted alkadienes to produce one or more substituted or unsubstituted alkenols is disclosed in copending U.S. patent application Ser. No. 08/842,666, filed Apr. 15, 1997, the disclosure of which is incorporated herein by reference. Another process involving the production of one or more substituted or unsubstituted alkenals and/or alkenols by hydroformylation and/or hydroformylation/hydrogenation is disclosed in copending U.S. patent application Ser. No. 08/843,389, filed Apr. 15, 1997, the disclosure of which is incorporated herein by reference.

The hydrocarbonylation processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The hydrocarbonylation processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the materials present during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. For example, hydrogen and carbon monoxide may be fed in appropriate mole ratios, e.g., about 2:1, to maintain desired partial pressures. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydrocarbonylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydrocarbonylation processes of this invention may be conducted in one or more steps or stages. The exact number of reaction steps or stages will be governed by the best compromise between achieving high catalyst selectivity, activity, lifetime and ease of operability, as well as the intrinsic reactivity of the starting materials in question and the stability of the starting materials and the desired reaction product to the reaction conditions.

The substituted and unsubstituted saturated alcohols produced by the processes of this invention can undergo further reaction(s) to afford desired derivatives thereof. Such permissible derivatization reactions can be carried out in accordance with conventional procedures known in the art. Illustrative derivatization reactions include, for example, halogenation, amination, alkylation, dehydration, acylation, condensation, oxidation, silylation and the like, including permissible combinations thereof This invention is not intended to be limited in any manner by the permissible derivatization reactions or permissible derivatives of substituted and unsubstituted saturated alcohols.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

Certain of the following examples are provided to further illustrate this invention.

EXAMPLES 1–10

A 100 milliliter overhead stirred high pressure reactor was charged with 0.25 mmol of dicarbonylacetylacetonato rhodium (I), about 0.95 mmol of phosphine indicated in Table A below, 3 milliliters of 1,3-butadiene, about 22 grams or 26 milliliters of solvent/promoter indicated in Table A, and 1 milliliter of digylme as internal standard. The reactor was pressurized with 5–10 psi of 1/1 hydrogen/carbon monoxide, and heated to about 80° C. At 80° C., the reactor was pressurized to 800 psi with 3/1 hydrogen/carbon monoxide and stirred for 90 minutes. The reactor gases were vented and the reaction mixture drained and analyzed by gas chromatography. The results are set out in Table A.

TABLE A

| Ex. No. | Ligand | Solvent/Promoter | Buta. Conv. % | Rate m/L/h | 1-Pentanol % |
|---|---|---|---|---|---|
| 1 | P(Octyl)$_3$ | Di(ethylene glycol) ethyl ether | 62 | >0.3 | 78 |
| 2 | P(Octyl)$_3$ | Methanol | 93 | 1.3 | 51 |
| 3 | P(CH$_2$Ph)$_3$ | Pyrrole | 87 | >1.0 | 38 |
| 4 | P(Octyl)$_3$ | Acetamide | 85 | 0.8 | 27 |
| 5 | P(Octyl)$_3$ | N-Methylacetamide | 73 | 0.5 | 20 |
| 6 | P(Octyl)$_3$ | Diphenylamine | 79 | 0.6 | 20 |
| 7 | P(Octyl)$_3$ | Diethyl-p-(N,N-di-Me-phenyl) phosphine | 66 | >0.3 | 24 |
| 8 | P(Octyl)$_3$ | EtOH/N,N,N,N-Tetra-Me-propanediamine | 86 | 1.4 | 29 |
| 9 | P(Octyl)$_3$ | THF/Phenol | 84 | 0.8 | 26 |
| 10 | P(Octyl)$_3$ | THF/Phenol | 73 | 0.4 | 65 |

Rates are reported at 20 minutes, and conversion and selectivities are reported at 90 minutes. Example 2 was conducted at a hydrogen partial pressure of 200 psi, a carbon monoxide partial pressure of 70 psi, and a temperature of 90° C. Example 3 was conducted at a hydrogen partial pressure of 200 psi and a carbon monoxide partial pressure of 600 psi.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for producing one or more substituted or unsubstituted saturated alcohols which comprises reacting one or more substituted or unsubstituted alkadienes with carbon monoxide and hydrogen in the presence of a homogeneous rhodium-ligand complex catalyst and a promoter and optionally free ligand to produce said one or more substituted or unsubstituted saturated alcohols, wherein said promoter comprises an organic or inorganic compound with an ionizable hydrogen of pKa of from about 1 to about 35.

2. A process for producing one or more substituted or unsubstituted saturated alcohols which comprises reacting one or more substituted or unsubstituted alkadienes with carbon monoxide and hydrogen in the presence of a homogeneous rhodium-organophosphorus ligand complex catalyst and a promoter and optionally free organophosphorus ligand to produce said one or more substituted or unsubstituted saturated alcohols, wherein said promoter comprises an organic or inorganic compound with an ionizable hydrogen of pKa of from about 1 to about 35.

3. A process for producing one or more substituted or unsubstituted 1-pentanols which comprises reacting one or more substituted or unsubstituted butadienes with carbon monoxide and hydrogen in the presence of a homogeneous rhodium-organophosphorus ligand complex catalyst and a promoter and optionally free organophosphorus ligand to produce said one or more substituted or unsubstituted 1-pentanols, wherein said promoter comprises an organic or inorganic compound with an ionizable hydrogen of pKa of from about 1 to about 35.

4. The process of claim 3 wherein the substituted or unsubstituted butadienes comprises butadiene and the substituted or unsubstituted 1-pentanols comprise 1-pentanol.

5. The process of claim 3 which is conducted at a hydrogen partial pressure and carbon monoxide partial pressure sufficient to prevent or minimize formation of substituted or unsubstituted lactols, diols and/or hydroxyaldehydes.

6. The process of claim 1 wherein said rhodium-ligand complex catalyst comprises rhodium complexed with an organophosphine ligand selected from a mono-, di-, tri- and poly-(organophosphine) ligand.

7. The process of claim 1 wherein said rhodium-ligand complex catalyst comprises rhodium complexed with an organophosphine ligand selected from a triorganophosphine ligand represented by the formula:

wherein each $R^1$ is the same or different and is a substituted or unsubstituted monovalent hydrocarbon radical.

8. The process of claim 7 wherein each $R^1$ is the same or different and is selected from primary alkyl, secondary alkyl, tertiary alkyl and aryl.

9. The process of claim 3 wherein the organophosphorus ligand has a basicity greater than or equal to the basicity of triphenylphosphine (pKb=2.74) and a steric bulk lower than or equal to a Tolman cone angle of 210°.

10. The process of claim 3 wherein the promoter is incorporated into the ligand structure either as the rhodium-ligand complex catalyst or as free ligand.

11. The process of claim 3 wherein the promoter has a pKa of about 1–35 and comprises a protic solvent, organic and inorganic acid, alcohol, water, phenol, thiol, selenol, nitroalkane, ketone, nitrile, amine, amide, or a mono-, di- or trialkylammonium salt or mixtures thereof.

12. The process of claim 3 which is conducted at a temperature from about 50° C. to 150° C. and at a total pressure from about 20 psig to about 3000 psig.

13. A process for producing a batchwise or continuously generated reaction mixture comprising:
  (1) one or more substituted or unsubstituted 1-pentanols;
  (2) optionally one or more substituted or unsubstituted cis-2-pentenols, trans-2-pentenols, cis-3-pentenols, trans-3-pentenols and/or 4-pentenols;
  (3) optionally one or more substituted or unsubstituted cis-2-pentenals, trans-2-pentenals, cis-3-pentenals, trans-3-pentenals and/or 4-pentenals;
  (4) optionally one or more substituted or unsubstituted valeraldehydes;
  (5) optionally one or more substituted or unsubstituted lactols, diols and/or hydroxyaldehydes, e.g., 2-methylvalerolactol, 2-ethylbutyrolactol, 2-methyl-1,5-pentanediol, 2-ethyl-1,4-butanediol, 1,6-hexanediol and 6-hydroxyhexanal; and
  (6) one or more substituted or unsubstituted butadienes, e.g., butadiene;
wherein the weight ratio of the sum of component (1) to the sum of components (2), (3), (4) and (5) is greater than about 0.1, preferably greater than about 0.25, more preferably greater than about 1.0; and the weight ratio of component (6) to the sum of components (1), (2), (3), (4) and (5) is about 0 to about 100, preferably about 0.001 to about 50;
which process comprises reacting one or more substituted or unsubstituted butadienes with carbon monoxide and hydrogen in the presence of a homogeneous rhodium-organophosphorus ligand complex catalyst and a promoter and optionally free organophosphorus ligand to produce said batchwise or continuously generated reaction mixture, wherein said promoter comprises an organic or inorganic compound with an ionizable hydrogen of pKa of from about 1 to about 35.

14. A process for producing a reaction mixture comprising one or more substituted or unsubstituted saturated alcohols which process comprises reacting one or more substituted or unsubstituted alkadienes with carbon monoxide and hydrogen in the presence of a homogeneous rhodium-ligand complex catalyst and a promoter and optionally free ligand to produce said reaction mixture comprising one or more substituted or unsubstituted saturated alcohols, wherein said promoter comprises an organic or inorganic compound with an ionizable hydrofgen of pKa of from about 1 to about 35.

15. A process for producing a reaction mixture comprising one or more substituted or unsubstituted 1-pentanols which process comprises reacting one or more substituted or unsubstituted butadienes with carbon monoxide and hydrogen in the presence of a homogeneous rhodium-organophosphorus ligand complex catalyst and a promoter and optionally free organophosphorus ligand to produce said reaction mixture comprising one or more substituted or unsubstituted 1-pentanols, wherein said promoter comprises an organic or inorganic compound with an ionizable hydrogen of pKa of from about 1 to about 35.

16. A batchwise or continuously generated reaction mixture comprising:
  (1) one or more substituted or unsubstituted 1-pentanols;
  (2) optionally one or more substituted or unsubstituted cis-2-pentenols, trans-2-pentenols, cis-3-pentenols, trans-3-pentenols and/or 4-pentenols;
  (3) optionally one or more substituted or unsubstituted cis-2-pentenals, trans-2-pentenals, cis-3-pentenals, trans-3-pentenals and/or 4-pentenals;
  (4) optionally one or more substituted or unsubstituted valeraldehydes;
  (5) optionally one or more substituted or unsubstituted lactols, diols and/or hydroxyaldehydes, e.g., 2-methylvalerolactol, 2-ethylbutyrolactol, 2-methyl-1-1,5-pentanediol, 2-ethyl-1-1,4-butanediol, 1,6-hexanediol and 6-hydroxyhexanal; and
  (6) one or more substituted or unsubstituted butadienes, e.g., butadiene;
wherein the weight ratio of the sum of component (1) to the sum of components (2), (3), (4) and (5) is greater than about 0.1, preferably greater than about 0.25, more preferably greater than about 1.0; and the weight ratio of component (6) to the sum of components (1), (2), (3), (4) and (5) is about 0 to about 100, preferably about 0.001 to about 50.

17. A reaction mixture comprising one or more substituted or unsubstituted saturated alcohols in which said reaction mixture is prepared by a process which comprises reacting one or more substituted or unsubstituted alkadienes with carbon monoxide and hydrogen in the presence of a homogeneous rhodium-ligand complex catalyst and a promoter and optionally free ligand to produce said reaction mixture comprising one or more substituted or unsubstituted saturated alcohols, wherein said promoter comprises an organic or inorganic compound with an ionizable hydrogen of pKa of from about 1 to about 35.

18. A reaction mixture comprising one or more substituted or unsubstituted 1-pentanols in which said reaction mixture is prepared by a process which comprises reacting one or more substituted or unsubstituted butadienes with carbon monoxide and hydrogen in the presence of a homogeneous rhodium-organophosphorus ligand complex catalyst and a promoter and optionally free organophosphorus ligand to produce said reaction mixture comprising one or more substituted or unsubstituted 1-pentanols, wherein said promoter comprises an organic or inorganic compound with an ionizable hydrogen of pKa of from about 1 to about 35.

19. The reaction mixture of claim 18 in which the process further comprises derivatizing said one or more substituted or unsubstituted 1-pentanols.

20. A derivative of the one or more substituted or unsubstituted 1-pentanols of claim 19.

* * * * *